United States Patent
Fuxman et al.

(10) Patent No.: US 11,631,475 B2
(45) Date of Patent: Apr. 18, 2023

(54) REAL-TIME PROJECTIONS AND ESTIMATED DISTRIBUTIONS OF AGRICULTURAL PESTS, DISEASES, AND BIOCONTROL AGENTS

(71) Applicant: Ecoation Innovative Solutions Inc., North Vancouver (CA)

(72) Inventors: Adrian M. Fuxman, North Vancouver (CA); Devin G. Kirk, Vancouver (CA); Eduardo Aparecido Sereguin Cabral de Melo, Vancouver (CA); Gregory E. Stewart, North Vancouver (CA)

(73) Assignee: Ecoation Innovative Solutions Inc., North Vancouver (CA)

( * ) Notice: Subject to any disclaimer, the term of this patent is extended or adjusted under 35 U.S.C. 154(b) by 388 days.

(21) Appl. No.: 16/883,354

(22) Filed: May 26, 2020

(65) Prior Publication Data
US 2021/0375390 A1   Dec. 2, 2021

(51) Int. Cl.
*G06Q 30/02* (2012.01)
*G16B 5/00* (2019.01)
(Continued)

(52) U.S. Cl.
CPC ............ *G16B 5/00* (2019.02); *A01N 61/00* (2013.01); *G06Q 10/04* (2013.01); *G06Q 50/02* (2013.01); *A01B 79/005* (2013.01)

(58) Field of Classification Search
CPC ........ G06Q 30/02; G06Q 10/04; G06Q 50/02; G06Q 30/0254; G06Q 10/067;
(Continued)

(56) References Cited

U.S. PATENT DOCUMENTS 4,755,942 A   7/1988   Gardner et al.
4,876,647 A   10/1989  Gardner et al.
(Continued)

FOREIGN PATENT DOCUMENTS

CN   102496077 A   6/2012
DE   10148747 A1   4/2003
(Continued)

OTHER PUBLICATIONS

Macedo, R;Sales, LP;Silva-Abud, LL;Lobo, MJ;Sarrocco, S, Potentil Worldwide distribution of furasium dry root rot in commen beans based on the optimal environment for disease occurence, PLoS ONE, 12(11), e0187779, Nov. 6, 2017 (Year: 2017).*
(Continued)

*Primary Examiner* — Marilyn G Macasiano

(57) ABSTRACT

An apparatus includes at least one processor configured to obtain multiple spatiotemporal population projection models. Different spatiotemporal population projection models are associated with different pests, diseases, or biocontrol agents in a growing area. Each spatiotemporal population projection model defines how the associated pest, disease, or biocontrol agent spreads and contracts in the growing area over time. The at least one processor is also configured to receive information associated with an actual presence of a specific pest, disease, or biocontrol agent at one or more locations in the growing area. Different locations in the growing area are associated with different plants. The at least one processor is further configured to project a future presence of the specific pest, disease, or biocontrol agent in the growing area using the spatiotemporal population projection model associated with the specific pest, disease, or biocontrol agent.

27 Claims, 8 Drawing Sheets

(51) Int. Cl.
  *A01N 61/00* (2006.01)
  *G06Q 10/04* (2023.01)
  *G06Q 50/02* (2012.01)
  *A01B 79/00* (2006.01)
(58) Field of Classification Search
  CPC .. G06Q 30/0246; G06Q 30/0207; G16B 5/00; A01N 61/00; A01B 79/005
  See application file for complete search history.

(56) References Cited

U.S. PATENT DOCUMENTS

| | | | |
|---|---|---|---|
| 5,130,545 | A | 7/1992 | Lussier |
| 5,839,106 | A | 11/1998 | Bellegarda |
| 5,884,224 | A * | 3/1999 | McNabb ............... A01G 7/00 700/284 |
| 6,385,544 | B1 | 5/2002 | Mafra-Neto |
| 6,397,162 | B1 | 5/2002 | Ton |
| 6,573,512 | B1 | 6/2003 | Lucia et al. |
| 6,657,117 | B2 | 12/2003 | Weare et al. |
| 6,701,665 | B1 | 3/2004 | Ton et al. |
| 7,112,806 | B2 | 9/2006 | Lussier |
| 7,412,330 | B2 | 8/2008 | Spicer et al. |
| 7,487,925 | B2 | 2/2009 | Skinner |
| 7,617,057 | B2 | 11/2009 | May et al. |
| 7,715,013 | B2 | 5/2010 | Glaser et al. |
| 7,987,632 | B2 | 8/2011 | May et al. |
| 8,028,470 | B2 | 10/2011 | Anderson |
| 8,061,080 | B2 | 11/2011 | Loebl et al. |
| 8,249,308 | B2 | 8/2012 | Lussier |
| 8,437,498 | B2 | 5/2013 | Malsam |
| 8,437,879 | B2 | 5/2013 | Anderson |
| 8,476,603 | B2 | 7/2013 | Moise et al. |
| 8,504,234 | B2 | 8/2013 | Anderson |
| 8,836,504 | B2 | 9/2014 | Kohler et al. |
| 9,532,411 | B2 | 12/2016 | Conrad et al. |
| 9,576,786 | B2 | 2/2017 | Greenberg et al. |
| 9,939,132 | B2 | 4/2018 | Greenberg et al. |
| 10,021,837 | B2 | 7/2018 | Greenberg et al. |
| 10,045,523 | B2 * | 8/2018 | Ehrlich ............... G06V 10/255 |
| 10,241,097 | B2 | 3/2019 | Miresmailli et al. |
| 10,339,380 | B2 | 7/2019 | Greenberg et al. |
| 10,577,103 | B2 * | 3/2020 | Cantrell ............... A01B 79/02 |
| 10,627,785 | B2 | 4/2020 | King et al. |
| 10,635,274 | B2 | 4/2020 | Greenberg et al. |
| 10,791,037 | B2 | 9/2020 | Greenberg et al. |
| 10,929,664 | B2 | 2/2021 | King |
| 10,949,974 | B2 | 3/2021 | King et al. |
| 11,003,456 | B2 | 5/2021 | King |
| 11,062,516 | B2 | 7/2021 | Greenberg et al. |
| 11,151,500 | B2 * | 10/2021 | Carroll ............... G06Q 10/0635 |
| 11,234,429 | B2 * | 2/2022 | Files ............... G06F 9/542 |
| 2002/0167587 | A1 | 11/2002 | Ogasawara |
| 2002/0170229 | A1 | 11/2002 | Ton et al. |
| 2003/0229497 | A1 | 12/2003 | Wilson et al. |
| 2004/0067850 | A1 * | 4/2004 | Wahlberg ............... A01N 37/44 504/116.1 |
| 2004/0241635 | A1 | 12/2004 | Buckley |
| 2011/0101239 | A1 | 5/2011 | Woodhouse et al. |
| 2011/0261355 | A1 | 10/2011 | Hannel et al. |
| 2012/0046837 | A1 | 2/2012 | Anderson |
| 2012/0101861 | A1 | 4/2012 | Lindores |
| 2012/0109387 | A1 | 5/2012 | Martin et al. |
| 2012/0114187 | A1 | 5/2012 | Duarte |
| 2012/0150355 | A1 | 6/2012 | Anderson |
| 2014/0035752 | A1 | 2/2014 | Johnson |
| 2014/0059722 | A1 | 2/2014 | Krichevsky |
| 2014/0064568 | A1 | 3/2014 | Moon et al. |
| 2014/0222374 | A1 | 8/2014 | Lock et al. |
| 2014/0311014 | A1 | 10/2014 | Feugier |
| 2016/0078570 | A1 | 3/2016 | Ethington et al. |
| 2017/0032258 | A1 | 2/2017 | Miresmailli et al. |
| 2017/0176595 | A1 | 6/2017 | McPeek |
| 2017/0332544 | A1 | 11/2017 | Conrad et al. |
| 2018/0082362 | A1 | 3/2018 | Greenberg et al. |
| 2018/0082375 | A1 | 3/2018 | Greenberg et al. |
| 2019/0170718 | A1 | 6/2019 | Miresmailli et al. |
| 2020/0160459 | A1 * | 5/2020 | Coolidge ............... G06Q 50/02 |
| 2020/0380616 | A1 | 12/2020 | King et al. |
| 2021/0298244 | A1 | 9/2021 | King et al. |
| 2021/0302973 | A1 | 9/2021 | King et al. |
| 2021/0304216 | A1 | 9/2021 | King et al. |
| 2021/0304326 | A1 | 9/2021 | Greenberg et al. |

FOREIGN PATENT DOCUMENTS

| | | | | |
|---|---|---|---|---|
| EP | 3491613 | A1 | 6/2019 | |
| JP | 6963102 | B2 | 11/2021 | |
| WO | 2009141465 | A1 | 11/2009 | |
| WO | 2015132208 | A1 | 9/2015 | |
| WO | WO 2015/132208 | A1 * | 9/2015 | ............ A01M 1/02 |
| WO | WO 2017/222722 | A1 * | 12/2017 | ............ A01B 79/02 |
| WO | 2018057799 | A1 | 3/2018 | |

OTHER PUBLICATIONS

Tangirala, Bhavesh; Laszlo,Daniel; Bhandari, Ishan; Gupta, Deepak, K; Thomas, Rajat, M.; Arya, Devanshu, Livestock monitoring with Transformer (English), Nov. 1, 2021 (Year: 2021).*
Jansen et al., "Induced plant volatiles allow sensitive monitoring of plant health status in greenhouses," Plant Signaling & Behavior, Sep. 2009, pp. 824-829.
Koppert Biological Systems, "Airbug," Produce Specification, Apr. 2020, 3 pages.
Koppert Biological Systems, "Biological pest management to ensure healthy crops," Product List, Dec. 2016, 1 page.
Mandow et al., "The Autonomous Mobile Robot AURORA for Greenhouse Operation," IEEE Robotics and Automation Magazine, Dec. 1996, 11 pages.
Nicolai et al., "Nondestructive measurement of fruit and vegetable quality by means of NIR spectroscopy: A review," Science Direct, Postharvest Biology and Technology 46, 2007, pp. 99-118.
Ruiz-Altisent et al., "Sensors for product characterization and quality of specialty crops—A review," Computers and Electronics in Agriculture 74, 2010, pp. 176-194.
Sankaran et al., "A review of advanced techniques for detecting plant diseases," Computer and Electronics in Agriculture, vol. 72, Jun. 2010, pp. 1-13.
Story et al., "Automated Machine Vision Guided Plant Monitoring System for Greenhouse Crop Diagnostics," ISHS Acta Horticulturae 1037, 2013, Abstract, 1 page.
Ton et al., "Phytomonitoring: A Bridge from Sensors to Information Technology for Greenhouse Control," Phytech Ltd., 2003, pp. 639-644.
Office Action dated Jul. 1, 2020 in connection with U.S. Appl. No. 16/268,744, 20 pages.
Office Action dated Mar. 11, 2020 in connection with U.S. Appl. No. 15/219,328, 21 pages.
Final Office Action dated Sep. 18, 2020 in connection with U.S. Appl. No. 15/219,328, 24 pages.
International Search Report and Written Opinion of the International Searching Authority dated Apr. 16, 2021 in connection with International Patent Application No. PCT/CA2021/050292, 15 pages.

* cited by examiner

REAL-TIME PROJECTIONS AND ESTIMATED DISTRIBUTIONS OF AGRICULTURAL PESTS, DISEASES, AND BIOCONTROL AGENTS

TECHNICAL FIELD

This disclosure is generally directed to plant monitoring and assessment. More specifically, this disclosure is directed to real-time projections and estimated distributions of agricultural pests, diseases, and biocontrol agents.

BACKGROUND

When plants are grown on a large scale, such as in protected cultivation (like a greenhouse) or outdoors, growers face various challenges. For example, it can be difficult for a grower to know if, when, where, and to what extent plants are suffering from problems related to pests and diseases. In many cases, the existence or extent of a problem is not known until it is readily visible to human scouts. By that time, resolving the problem may require expensive and extensive intervention.

SUMMARY

This disclosure relates to real-time projections and estimated distributions of agricultural pests, diseases, and biocontrol agents.

In a first embodiment, an apparatus includes at least one processor configured to obtain multiple spatiotemporal population projection models. Different spatiotemporal population projection models are associated with different pests, diseases, or biocontrol agents in a growing area. Each spatiotemporal population projection model defines how the associated pest, disease, or biocontrol agent spreads and contracts in the growing area over time. The at least one processor is also configured to receive information associated with an actual presence of a specific pest, disease, or biocontrol agent at one or more locations in the growing area. Different locations in the growing area are associated with different plants. The at least one processor is further configured to project a future presence of the specific pest, disease, or biocontrol agent in the growing area using the spatiotemporal population projection model associated with the specific pest, disease, or biocontrol agent.

In a second embodiment, a non-transitory computer readable medium contains instructions that when executed cause at least one processor to obtain multiple spatiotemporal population projection models. Different spatiotemporal population projection models are associated with different pests, diseases, or biocontrol agents in a growing area. Each spatiotemporal population projection model defines how the associated pest, disease, or biocontrol agent spreads and contracts in the growing area over time. The medium also contains instructions that when executed cause the at least one processor to receive information associated with an actual presence of a specific pest, disease, or biocontrol agent at one or more locations in the growing area. Different locations in the growing area are associated with different plants. The medium further contains instructions that when executed cause the at least one processor to project a future presence of the specific pest, disease, or biocontrol agent in the growing area using the spatiotemporal population projection model associated with the specific pest, disease, or biocontrol agent.

In a third embodiment, a method includes obtaining multiple spatiotemporal population projection models. Different spatiotemporal population projection models are associated with different pests, diseases, or biocontrol agents in a growing area. Each spatiotemporal population projection model defines how the associated pest, disease, or biocontrol agent spreads and contracts in the growing area over time. The method also includes receiving information associated with an actual presence of a specific pest, disease, or biocontrol agent at one or more locations in the growing area. Different locations in the growing area are associated with different plants. The method further includes projecting, using at least one processing device, a future presence of the specific pest, disease, or biocontrol agent in the growing area using the spatiotemporal population projection model associated with the specific pest, disease, or biocontrol agent.

Other technical features may be readily apparent to one skilled in the art from the following figures, descriptions, and claims.

BRIEF DESCRIPTION OF THE DRAWINGS

For a more complete understanding of this disclosure and its features, reference is now made to the following description, taken in conjunction with the accompanying drawings, in which.

DETAILED DESCRIPTION

Figure 1:
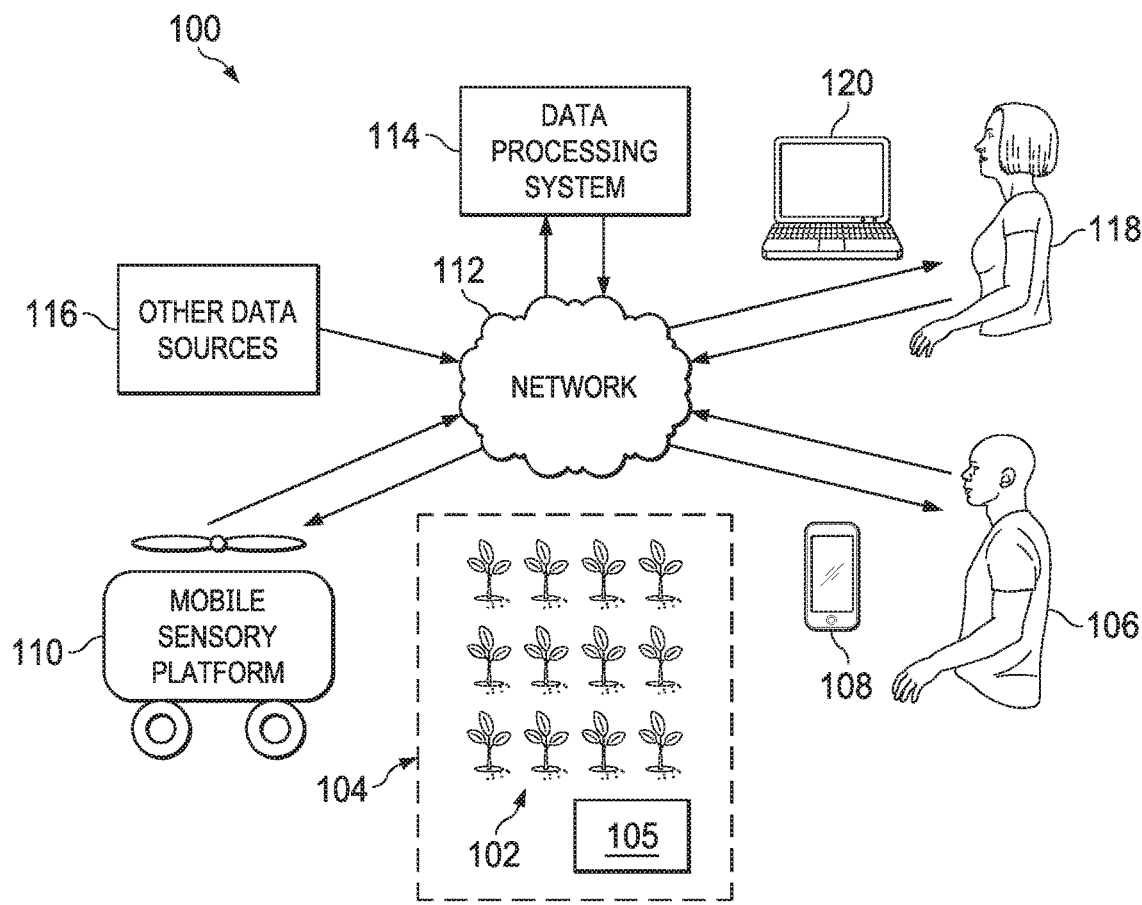
FIG. 1 illustrates an example system for real-time projections and estimated distributions of agricultural pests, diseases, and biocontrol agents according to this disclosure.

FIGS. 1 through 5, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, when plants are grown on a large scale, growers face various challenges. For example, it can be difficult for a grower to know if, when, where, and to what extent plants are suffering from problems related to pests, diseases, or other problems. In many cases, the existence or extent of a problem is not known until it is readily visible to human scouts, at which point resolving the problem may require expensive and extensive intervention.

Effective pest and disease management typically involves diligently scouting for pests and diseases, assessing real and potential damage caused by the pests and diseases, assessing costs versus benefits of treatment options for the pests and diseases, and diligently applying those treatments. Scouting today is often a manual activity, and full scouting or inspection coverage of a growing area is often achieved over a prolonged period of time (such as every two to five weeks). This means that each plant in a given area may be inspected by a scout only once during that prolonged period of time. This prolonged latency time may allow pests or diseases to become established in the given area, which makes treatment of the pests or diseases more difficult, time consuming, and expensive.

This disclosure provides various techniques for real-time projections and estimated distributions of agricultural pests, diseases, and biocontrol agents in one or more growing areas, such as in protected cultivation (like a greenhouse) or outdoors. As described below, these techniques use observations from human or robotic scouts at various locations in one or more growing areas along with spatiotemporal population projection modeling to generate projections of how pests, diseases, and possibly biocontrol agents may spread and be distributed in the future. These projections and estimated distributions can be provided to human or robotic scouts in order to help the scouts look for specific pests, diseases, and biocontrol agents at specific locations in the one or more growing areas. These projections and estimated distributions may also be used by human or machine-based decision makers for use in deciding what treatments (if any) should be applied at specific locations in the one or more growing areas. These projections and estimated distributions may be used in various other or additional ways, as well.

Among other things, these techniques may generate and provide a full coverage map of an entire growing area for pest and disease risks much more frequently, such as on a daily basis. This gives growers improved ability to identify pests and diseases and project their spread in an entire greenhouse or other growing area much more frequently than a typical two- to five-week inspection routine. Also, this allows on-location notifications or alerts to be provided to scouts, where the notifications or alerts are related to risk levels for specific pests or diseases in the vicinity of the scouts. This helps to enhance the performance of the scouts since the scouts now have advanced knowledge of potential problems in specific parts of a growing area. This can also permit a grower to use less-trained scouts and to extend their scouting labor pool, since the training of an expert scout may require a very long period of time (such as about five years). Further, the projections and estimated distributions can provide information and assistance to growers in determining improved or optimal times for applying interventions, and they can help to prioritize the interventions based on risk or pressure maps or other data processing results. In addition, models of pests and diseases are often used as input elements to crop productivity forecasting. Often times, crop yield is a function of various factors like outdoor climate (such as amount of solar radiation), indoor climate (such as $CO_2$ level, vapor-pressure deficit, and artificial lighting), crop work (such as lowering and/or deleafing of plants, fertilization, irrigation, and patterns of human movement), and pest/disease-related information (such as pest and disease pressures and treatments) over at least the past several weeks. Thus, the availability of projections and estimated distributions related to pests, diseases, and biocontrol agents can help to improve the accuracy of crop productivity forecasting.

In this patent document, the term "pests" generally refers to animals or plants that are detrimental to the growth or well-being of plants in a specified area. Pests can include ectoparasites such as certain types of insects, mites, and vertebrates. Specific examples of pests can include whiteflies, aphids, thrips, spider mites, mealybugs, caterpillars, sciarid flies, shore flies, leaf miners, vine weevils, red palm weevils, and white grubs. The term "diseases" generally refers to pathogens that are detrimental to the growth or well-being of plants in a specified area. Specific examples of diseases may include certain types of bacteria, viruses, fungi, oomycetes, protozoa, and nematodes. The phrase "beneficial organisms" generally refers to living organisms that are beneficial to the growth or well-being of plants in a specified area, such as organisms that attack or reduce pests or diseases. Specific examples of beneficial organisms may include certain types of parasitic wasps, predatory mites, beetles (such as ladybugs and ladybirds), fungi, and nematodes. Plants in a specified area may be subjected to various "treatments," "interventions," or "biocontrol agents" to help combat pests and diseases. Treatments, interventions, and biocontrol agents can include the application or use of beneficial organisms, insecticidal soaps (such as one containing a potassium salt of fatty acids), or chemical insecticides or other chemical treatments. Note that the examples provided above are merely for illustration only and that other pests, diseases, beneficial organisms, and treatments/interventions/biocontrol agents may exist in any given implementation.

FIG. 1 illustrates an example system 100 for real-time projections and estimated distributions of agricultural pests, diseases, and biocontrol agents according to this disclosure. As shown in FIG. 1, the system 100 is used to monitor and assess the condition of various plants 102 being grown in one or more growing areas 104. The plants 102 represent any suitable plants being grown and whose condition is monitored and assessed, and the plants 102 may be used for any suitable purposes. For example, the plants 102 may represent crops that provide food for people or animals, crops that provide material for industrial or medicinal purposes, or flowers or other ornamental plants. In general, the system 100 may be used to monitor and assess any suitable type(s) of plant(s) 102, including a single type of plant 102 or multiple types of plants 102. The system 100 may also be used to monitor and assess any suitable number of plants 102.

Each growing area 104 represents any suitable space in which the plants 102 can be grown, monitored, and assessed. For example, in some embodiments, each growing area 104 may represent a greenhouse or other protected cultivation area or a portion thereof. Protected cultivation technology is generally used to provide favorable climatic conditions for one or more specific types of plants 102, which can vary based on the specific plants 102 being grown. These favorable climatic conditions can reduce stress levels on the plants 102 and help increase yields obtained from the plants 102. In other embodiments, each growing area 104 may represent an open field or other outdoor or unprotected area or a portion thereof. In general, the system 100 may be used to monitor and assess plants 102 in any suitable type(s) of growing area(s) 104, including a single type of growing area 104 or multiple types of growing areas 104. The system 100 may also be used to monitor and assess plants 102 in any suitable number of growing areas 104.

Note that each growing area 104 may optionally include one or more types of equipment 105 used to help facilitate growth of the plants 102. For example, each growing area 104 may include irrigation equipment configured to provide water to the plants 102 and, if necessary, drainage equipment configured to handle water that is not retained by the plants 102 or their associated containers (if any). Each growing area 104 may also include nutrition equipment configured to provide nutritional materials to the plants 102. At least part of the nutrition equipment might be integrated into or with the irrigation equipment so that at least some of the nutritional materials can be provided to the plants 102 via the water that is provided to the plants 102. Each growing area 104 may further include lighting equipment configured to provide artificial lighting or to control natural lighting provided to the plants 102. Each growing area 104 may also include temperature equipment configured to create a desired temperature or temperature range around the plants 102. Each growing area 104 may further include humidity equipment configured to create a desired humidity or humidity range around the plants 102. Each growing area 104 may also include carbon dioxide ($CO_2$) equipment configured to create a desired $CO_2$ level or $CO_2$ range around the plants 102. In addition, each growing area 104 may include pruning, spraying, and/or harvesting equipment used to physically prune the plants 102, spray insecticide or other materials onto the plants 102, and/or harvest the plants 102 or portions thereof. In general, the system 100 may use any suitable type(s) of equipment 105 in the growing area(s) 104 to perform any desired operation(s) involving the plants 102. Note that the specific equipment 105 used here can vary based on a number of factors, such as based on the specific types of plants 102 and whether the plants 102 are grown indoors or outdoors.

In many cases, the plants 102 in the one or more growing areas 104 are arranged in a specified pattern. For example, the plants 102 in each growing area 104 may typically be arranged in long rows of plants 102, where the rows are spaced apart from one another. This helps to provide space for people or objects to move between the plants 102 and to ensure that each plant 102 receives adequate lighting, air flow, moisture, etc. If used in a greenhouse, for example, each plant 102 or group of plants 102 may be placed into a suitable container, and the containers may be arranged in rows in order to facilitate easy movement of the plants 102 as needed or desired. In some instances, the containers themselves may be raised off the ground using suitable holders, which may help to facilitate improved drainage of the containers or to reduce to ability of pests to easily reach the containers.

One or more human scouts 106 are often employed to walk or ride around the one or more growing areas 104 and to manually inspect the plants 102. For example, each human scout 106 may visually inspect various plants 102 in order to identify any visible signs of pests, diseases, over- or under-watering, malnutrition, or other problems associated with the plants 102. As another example, each human scout 106 may visually inspect various plants 102 in order to identify any beneficial organisms present on or near the plants 102. As yet another example, each human scout 106 may carry one or more instruments that can be used to perform instrument-based inspections of the plants 102. As still another example, each human scout 106 may use or have access to a cart or other portable equipment that carries one or more instruments that can be used to perform instrument-based inspections of the plants 102.

In this example, each human scout 106 may carry or otherwise have access to a tablet computer or other mobile electronic device 108, which the human scout 106 may use to provide or retrieve data. For example, each human scout 106 may use a mobile electronic device 108 to capture still or video images of plants 102 being inspected, identify any pests/diseases/other conditions associated with the plants 102 being inspected, or identify any beneficial organisms associated with the plants 102 being inspected.

Each mobile electronic device 108 may also identify its location in order to associate captured information or to provide useful information related to one or more plants 102 at or near its location. For example, a mobile electronic device 108 may identify its location and associate any information input by a human scout 106 with that location. This may allow, for instance, the mobile electronic device 108 to automatically associate information input by the human scout 106 with that location or with one or more plants 102 at or near that location. As another example, a mobile electronic device 108 may identify its location and output to a human scout 106 any pests or diseases previously identified at or near its location or any pests or diseases projected to now exist at or near its location. Note, however, that in other embodiments the identification of the location of a mobile electronic device 108 may occur in another component external to the mobile electronic device 108, in which case the external component may be responsible for associating captured information with the mobile electronic device's location or for providing information based on the mobile electronic device's location.

Any suitable technique may be used to identify a location of each mobile electronic device 108, such as manual input from a user, the use of Global Positioning System (GPS) or Ultra-Wideband (UWB) positioning, the scanning of optical tags (such as bar codes or QR codes), or the transmission or receipt of radio frequency identification (RFID) signals or other wireless signals. Note that this disclosure is not limited to any particular location identification technique. The specific location identification technique(s) used in the system 100 can vary as needed or desired, and a location identification technique may be used within or external to the mobile electronic devices 108.

One or more mobile sensory platforms 110 (also referred to as robotic scouts 110) may also or alternatively be employed to move around the one or more growing areas 104 and to automatically inspect the plants 102. For example, each robotic scout 110 may include one or more cameras for capturing still or video images of plants 102 being inspected, one or more sensors for measuring one or more aspects associated with the plants 102 being inspected, or other components configured to collect measurement data associated with the plants 102 being inspected. Each robotic scout 110 may include any suitable type(s) of sensor(s) or other measurement device(s), such as one or more physiological sensors, surface analysis sensors, chemical sensors, thermal sensors, microclimate sensors, image-based or video-based sensors, spectroscopy sensors, volatile organic compound sensors, or canopy scanning sensors. Note that the same type(s) of sensor(s) may also or alternatively be used by the human scouts 106.

Each robotic scout 110 may also identify its location or engage in actions that allow an external component to identify its location. Any suitable technique may be used by each robotic scout 110 or another component to identify a location of the robotic scout 110. Example techniques may include the use of GPS or UWB positioning, the scanning of optical tags (such as bar codes or QR codes), or the transmission or receipt of RFID signals or other signals. Again, note that this disclosure is not limited to any particular location identification technique(s), and a location identification technique may be used within or external to each robotic scout 110.

Any suitable type(s) of robotic scout(s) 110 may be used in the system 100 to automatically inspect plants 102 in one or more growing areas 104. In some embodiments, example implementations of the robotic scouts 110 are provided in U.S. Pat. No. 10,241,097 and U.S. Patent Application Publication No. 2017/0032258 (both of which are hereby incorporated by reference in their entirety). Note, however, that this disclosure is not limited to use with any particular type of robotic scout 110.

At least one network 112 facilitates communication between various components of the system 100. For example, the network 112 may communicate Internet Protocol (IP) packets, frame relay frames, Asynchronous Transfer Mode (ATM) cells, or other suitable information between network addresses. The network 112 may include one or more local area networks (LANs), metropolitan area networks (MANs), wide area networks (WANs), all or a portion of a global network such as the Internet, or any other communication system or systems at one or more locations. The network 112 may also operate according to any appropriate communication protocol or protocols. In some cases, the network 112 may include at least one wireless network that facilitates wireless communications with the mobile electronic devices 108 and the robotic scouts 110, as well as at least one wired network that facilitates wired communications.

A data processing system 114 is coupled to the network 112 and is configured to process data collected by the mobile electronic devices 108 and/or the robotic scouts 110. The data processing system 114 can also interact with the mobile electronic devices 108 and the robotic scouts 110, such as by providing data to the mobile electronic devices 108 for use by the human scouts 106 and by providing data to the robotic scouts 110 to control scouting. As described in more detail below, for example, the data processing system 114 processes data associated with pests, diseases, or other problems identified by the human scouts 106 and/or the robotic scouts 110. The data processing system 114 may also optionally process any data associated with beneficial organisms or other biocontrol agents identified by the human scouts 106 and/or the robotic scouts 110 or applied to the plants 102. The data processing system 114 may further optionally process any data associated with climate or other characteristics associated with the plants 102. Based on this processing, the data processing system 114 generates projections regarding the pests, diseases, or other problems in order to estimate how the pests, diseases, or other problems might spread or contract in the future (which can be affected by the climate and/or the biocontrol agents if any). The data processing system 114 may further communicate its projections or estimated distributions of pests and diseases to the mobile electronic devices 108 and/or the robotic scouts 110. This may cause the human scouts 106 and/or the robotic scouts 110 to inspect certain parts of the one or more growing areas 104 more frequently or to pay special attention for specific pests or diseases in certain parts of the one or more growing areas 104. Example operations that may be performed by the data processing system 114 are described in more detail below.

Figure 2:
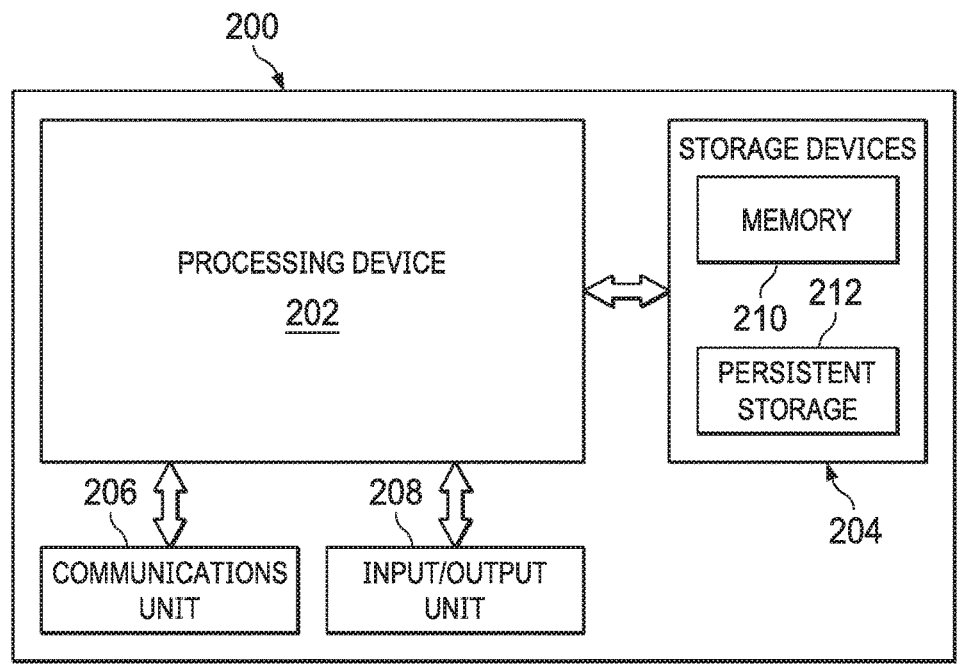
FIG. 2 illustrates an example device for real-time projections and estimated distributions of agricultural pests, diseases, and biocontrol agents according to this disclosure.

The data processing system 114 includes any suitable structure configured to process plant-related data and to generate projections and estimated distributions of pests or diseases in one or more growing areas. For example, the data processing system 114 may represent at least one desktop computer, laptop computer, server computer, or other computing device. Note that the data processing system 114 may be local to or remote from the one or more growing areas 104. In some cases, for instance, the data processing system 114 may be implemented in a cloud-based environment or using one or more remote servers. Among other things, this may allow a service provider to provide its data processing capabilities to a number of growers over a small or wide geographic area. One example of the data processing system 114 is shown in FIG. 2, which is described below.

In some cases, the data processing system 114 may receive and process data obtained from one or more other data sources 116, which represent data sources separate from the human and robotic scouts 106, 110. These data sources 116 may represent any other suitable source(s) of data related to the growing of the plants 102. For example, the data sources 116 may include one or more fixed sensors located at one or more points in or around the one or more growing areas 104. These fixed sensors may be used to collect any suitable information, such as natural or artificial lighting conditions, humidity, or other conditions that affect multiple plants 102 or multiple growing areas 104. The data sources 116 may also or alternatively include external sources of information, such as predicted near-term weather or predicted long-term climate conditions.

Also, in some cases, the data processing system 114 may communicate with one or more additional users 118, who may use one or more electronic devices 120. The additional users 118 may represent any suitable users associated with the plants 102 or the growing areas 104, such as one or more experts, non-experts, growers, or crop-site managers. The electronic devices 120 may represent any suitable electronic devices for interacting with the data processing system 114, such as desktop computers, laptop computers, tablet computers, or mobile smartphones. The users 118 and their electronic devices 120 may be located local to or remote from the one or more growing areas 104.

Although FIG. 1 illustrates one example of a system 100 for real-time projections and estimated distributions of agricultural pests, diseases, and biocontrol agents, various changes may be made to FIG. 1. For example, the system 100 may include any suitable number of plants 102 in any suitable number of growing areas 104, and the plants 102 may be inspected by any suitable number of human scouts 106 and/or robotic scouts 110. Also, the system 100 may include any suitable number of networks 112, data processing systems 114, and other data sources 116, and the system 100 may interact with any suitable number of additional users 118.

FIG. 2 illustrates an example device 200 for real-time projections and estimated distributions of agricultural pests, diseases, and biocontrol agents according to this disclosure. One or more instances of the device 200 may, for example, be used to at least partially implement the functionality of the data processing system 114 of FIG. 1. However, the functionality of the data processing system 114 may be implemented in any other suitable manner. Also, the same or similar arrangement of components as shown in FIG. 2 may be used to at least partially implement the functionality of one or more of the electronic devices 108, 120 in FIG. 1. However, the functionality of each electronic device 108, 120 may be implemented in any other suitable manner. In addition, the same or similar arrangement of components as shown in FIG. 2 may be used to at least partially implement the functionality of each robotic scout 110 in FIG. 1. However, the functionality of each robotic scout 110 may be implemented in any other suitable manner.

As shown in FIG. 2, the device 200 denotes a computing device or system that includes at least one processing device 202, at least one storage device 204, at least one communications unit 206, and at least one input/output (I/O) unit 208. The processing device 202 may execute instructions that can be loaded into a memory 210. The processing device 202 includes any suitable number(s) and type(s) of processors or other devices in any suitable arrangement. Example types of processing devices 202 include one or more microprocessors, microcontrollers, digital signal processors (DSPs), application specific integrated circuits (ASICs), field programmable gate arrays (FPGAs), or discrete circuitry.

The memory 210 and a persistent storage 212 are examples of storage devices 204, which represent any structure(s) capable of storing and facilitating retrieval of information (such as data, program code, and/or other suitable information on a temporary or permanent basis). The memory 210 may represent a random access memory or any other suitable volatile or non-volatile storage device(s). The persistent storage 212 may contain one or more components or devices supporting longer-term storage of data, such as a read only memory, hard drive, Flash memory, or optical disc.

The communications unit 206 supports communications with other systems or devices. For example, the communications unit 206 can include a network interface card or a wireless transceiver facilitating communications over a wired or wireless network, such as the network 112. The communications unit 206 may support communications through any suitable physical or wireless communication link(s).

The I/O unit 208 allows for input and output of data. For example, the I/O unit 208 may provide a connection for user input through a keyboard, mouse, keypad, touchscreen, or other suitable input device. The I/O unit 208 may also send output to a display, printer, or other suitable output device. Note, however, that the I/O unit 208 may be omitted if the device 200 does not require local I/O, such as when the device 200 can be accessed remotely.

In some embodiments, the instructions executed by the processing device 202 can include instructions that implement the functionality of the data processing system 114. For example, the instructions executed by the processing device 202 can cause the processing device 202 to analyze data collected about various plants 102, such as data from one or more human scouts 106 (via one or more mobile electronic devices 108) and/or one or more robotic scouts 110 and optionally data from one or more other data sources 116. The instructions executed by the processing device 202 can also cause the processing device 202 to apply one or more spatiotemporal population projection models to the data in order to project the presence and estimate the distribution of one or more pests or diseases in one or more growing areas 104 for some future time period. A spatiotemporal population projection model generally refers to a model that is often expressed as a mathematical formula. The mathematical formula is used to project in the future (thus the "projection") how a population of a pest, disease, or biocontrol agent can spread (thus the "population") in a growing area 104 spatially over time (thus the "spatiotemporal"). The instructions executed by the processing device 202 can further cause the processing device 202 to output the projections and estimated distributions of the pests or diseases, such as by providing the projections and distributions to one or more human scouts 106 (via one or more mobile electronic devices 108), one or more robotic scouts 110, and/or one or more additional users 118 (via one or more electronic devices 120). The instructions executed by the processing device 202 may also or alternatively cause the processing device 202 to use the projections and estimated distributions in any other suitable manner, such as by using the projections and estimated distributions as inputs to a crop productivity forecasting application or by using the projections and estimated distributions to automatically initiate one or more treatments of one or more plants 102 or one or more growing areas 104 or to identify one or more treatments of one or more plants 102 or one or more growing areas 104 that can be performed manually. One or more treatments may be automatically applied to the plant(s) 102 using, for instance, one or more robotic scouts 110 or one or more actuators in the equipment 105 in a growing area 104 that can be initiated or controlled by the data processing system 114. One specific example of a type of actuator that may be used here is the AIRBUG distribution device from KOPPERT BIOLOGICAL SYSTEMS.

The one or more spatiotemporal population projection models that are applied to the collected data can have various forms depending on the implementation. However, a spatiotemporal population projection model will typically allow growth to occur in a pest or disease pressure at each location of a growing area 104 until the pressure convergences to a maximum permitted value. Here, "pressure" generally refers to a measure of how bad a pest or disease presence is in a given location of a growing area 104. Pressure can be expressed in various ways, such as different amounts of pest or disease (like low, medium, and high) or different amounts of expected damage. The maximum permitted value is used to represent the fact that pest or disease pressure eventually reaches a maximum value, since the presence of the pest or disease cannot increase infinitely. A spatiotemporal population projection model will also typically consider one or more neighboring locations when estimating the pest or disease pressure at each location of a growing area 104, which helps to account for spread of the pest or disease. A spatiotemporal population projection model will further typically consider an estimated speed at which a pest or disease can spread. In addition, a spatiotemporal population projection model will typically consider the overall rate at which the pest or disease pressure is changing (increasing or decreasing) for an entire growing area 104 (rather than just at specific individual locations within the growing area 104).

In some embodiments, a spatiotemporal population projection model used by the data processing system 114 for a specific pest or disease in a specific growing area 104 may have the following form:

$$P(x,y,t+1)=P(x,y,t)+(1-P(x,y,t)/P_{max}(x,y))\times(\beta\times dP_{mean}/dt\times\text{Sum}_{kNN}P(x,y,t)) \quad (1)$$

Here, the index (x,y) represents a specific spatial location in the specific growing area 104, such as the $x^{th}$ row and $y^{th}$ plant post in a greenhouse or other growing area 104. Also, P(x,y,t) represents a pest or disease pressure at the specific (x,y) spatial location for a given time t (such as today) in the specific growing area 104, and P(x,y,t+1) represents the estimated pest or disease pressure at the specific (x,y) spatial location for a given future time step t+1 (such as tomorrow) in the specific growing area 104. The value $P_{max}(x,y)$ represents the maximum carrying capacity of the pest or disease at the specific (x,y) spatial location in the specific growing area 104, and β represents a growth parameter that defines how quickly the pest or disease can grow and spread in the specific growing area 104. The value $dP_{mean}/dt$ refers to the rate of overall change (increase or decrease) in the observed pressures in at least nearby spatial locations of the specific growing area 104 (and possibly in the entire growing area 104), which helps to inform the model whether a pest or disease is increasing (growing) or decreasing (such as due to a treatment). In addition, the value $\text{Sum}_{kNN}P(x,y,t)$ is a function that collects neighboring pest or disease pressures relative to the specific (x,y) spatial location, meaning the model projection has the effect of spreading the pest or disease pressure from one spatial location to nearby spatial locations.

The model defined in Equation (1) can be implemented for a specific pest/disease in a specific growing area 104 by identifying only two parameters, namely the value of β and the range of neighboring spatial locations to be used in the function $\text{Sum}_{kNN} P(x,y,t)$ (in other words, how far the pest or disease pressure in one spatial location is propagated to neighboring spatial locations in each time step). The model defined in Equation (1) can be used for different pests and diseases and for different growing areas 104, although the β and $\text{Sum}_{kNN} P(x,y,t)$ parameters can be defined or tailored specifically for those different pests/diseases and growing areas 104.

To commission each model, the value of β and the range of neighboring spatial locations to be used in the function $\text{Sum}_{kNN} P(x,y,t)$ can be determined to have appropriate values for a combination of a specific pest or disease in a specific growing area 104, such as a specific greenhouse. In some cases, the commissioning of a model for a specific pest or disease can be based on historical measurements of that specific pest or disease in that specific growing area 104, such as prior human or robotic measurements related to the amount and the spread of the specific pest or disease over time in the specific growing area 104. The commissioning of the model for the specific pest or disease in the specific growing area 104 can involve selecting theft and $\text{Sum}_{kNN} P(x,y,t)$ parameters so that the model generates projections based on the historical data that provide the smallest error between the projections and the actual historical measurements. This is often referred to in other fields as "model identification" and generally involves optimizing the β and $\text{Sum}_{kNN} P(x,y,t)$ parameters so that the model projects the behavior of the specific pest or disease over time based on the historical data with little or no error.

The model shown in Equation (1) may be expanded in various ways to account for other data that might be available to the data processing system 114. For example, the model shown in Equation (1) may be expanded to account for one or more treatments applied to the pest or disease associated with the model. In some embodiments, a spatiotemporal population projection model used by the data processing system 114 for a specific pest or disease in a specific growing area 104 that accounts for a treatment may have the following form:

$$P(x,y,t+1)=P(x,y,t)+(1-P(x,y,t)/P_{max}(x,y))\times(\beta \times dP_{mean}/dt \times \text{Sum}_{kNN}P(x,y,t))+\gamma \times \text{Treatment}(x,y,t) \quad (2)$$

Here, the γ×Treatment(x,y,t) parameter refers to the impact of a specific treatment applied at the (x,y) spatial location in the specific growing area 104 at time t. To commission the version of the model shown in Equation (2), part of the collected historical measurements may identify how the specific pest or disease previously responded to a specific treatment in the specific growing area 104 or in other growing areas 104.

As another example, the model shown in Equation (1) may be expanded to account for the climate in a greenhouse or other specific growing area 104. In some embodiments, a spatiotemporal population projection model used by the data processing system 114 for a specific pest or disease in a specific growing area 104 that accounts for climate may have the following form:

$$P(x,y,t+1)=P(x,y,t)+(1-P(x,y,t)/P_{max}(x,y))\times(\beta(\text{Climate})\times dP_{mean}/dt \times \text{Sum}_{kNN}P(x,y,t)) \quad (3)$$

Here, the β parameter is dependent on the climate in the growing area 104 since, for instance, pests and diseases can often spread faster or slower depending on the climate. To commission the version of the model shown in Equation (3), part of the collected historical measurements can identify how the specific pest or disease previously spread under different climatic conditions in the specific growing area 104 or in other growing areas 104.

A combination of treatments and climate can also be considered by each model. In some embodiments, a spatiotemporal population projection model used by the data processing system 114 for a specific pest or disease in a specific growing area 104 that accounts for treatment and climate may have the following form:

$$P(x,y,t+1)=P(x,y,t)+(1-P(x,y,t)/P_{max}(x,y))\times(\beta(\text{Climate})\times dP_{mean}/dt \times \text{Sum}_{kNN}P(x,y,t))+\gamma \times \text{Treatment}(x,y,t) \quad (4)$$

Note that the models defined in Equations (1)-(4) above are examples only, and other spatiotemporal population projection models may be used by the data processing system 114. For example, spatiotemporal population projection models that separate the growth and migration parameters may be used. Also note that the commissioning of each model used by the data processing system 114 may occur using the data processing system 114 (such as in response to commands provided by one or more users 118) or using another device or system (such as an electronic device 120). In general, models may be commissioned by any suitable device(s) and in any suitable manner. If not commissioned by the data processing system 114, the models that result from the commissioning may be provided to the data processing system 114 for use.

As noted above, the forms of the models defined in Equations (1)-(4) may be consistent for all pests and diseases being monitored. However, the β and $\text{Sum}_{kNN} P(x,y,t)$ parameters in the models will often differ depending on the specific pest or disease. Also, the β and $\text{Sum}_{kNN} P(x,y,t)$ parameters in the models will often differ for the same pest or disease in different greenhouses or other growing areas 104. As a result, model identification may need to occur for each pest or disease in each growing area 104. Further, various pest- or disease-specific model structures may be supported by the data processing system 114, such as when the β and $\text{Sum}_{kNN} P(x,y,t)$ parameters in the models can differ depending on the type of pest or disease. As a particular example, it is possible that winged pests can spread more uniformly in a specific growing area 104, while legged pests tend to follow the rows of plants 102 and are slower to cross gaps between the rows of plants 102 in the specific growing area 104.

As discussed above, these types of spatiotemporal population projection models may allow growth to occur in a pest or disease pressure at each location of a growing area 104 until the pressure converges to a maximum permitted value. This may be referred to as logistic growth, where the growth may initially increase exponentially but then slows as the population of a pest or disease approaches a maximum value. These types of spatiotemporal population projection models account for pest/disease pressure increases and decreases at various spatial locations in a growing area 104 while also taking into account what happens at least in nearby (and possibly all) spatial locations in the growing area 104. Thus, the collective or overall pest or disease pressure may remain relatively constant if decreases in pressure at some spatial locations are offset by increases in pressure at other spatial locations.

Note that while described above as being used to identify pest and disease pressures in specific growing areas 104, the same approach can be used to identify the growth of beneficial organisms in specific growing areas 104. Thus, for example, the same types of equations as shown in Equations (1)-(4) above can be used by the data processing system 114 to identify pressures of beneficial organisms used in specific growing areas 104. Here, the "pressure" of a beneficial organism generally refers to a measure of how good a beneficial organism's presence is in a given location of a growing area 104. These models can be commissioned in the same way as the other models.

Although FIG. 2 illustrates one example of a device 200 for real-time projections and estimated distributions of agricultural pests, diseases, and biocontrol agents, various changes may be made to FIG. 2. For example, computing devices/systems, mobile electronic devices, and robotic scouts can come in a wide variety of configurations, and FIG. 2 does not limit this disclosure to any particular computing device or system, to any particular mobile electronic device, or to any particular robotic scout.

Figure 3A:
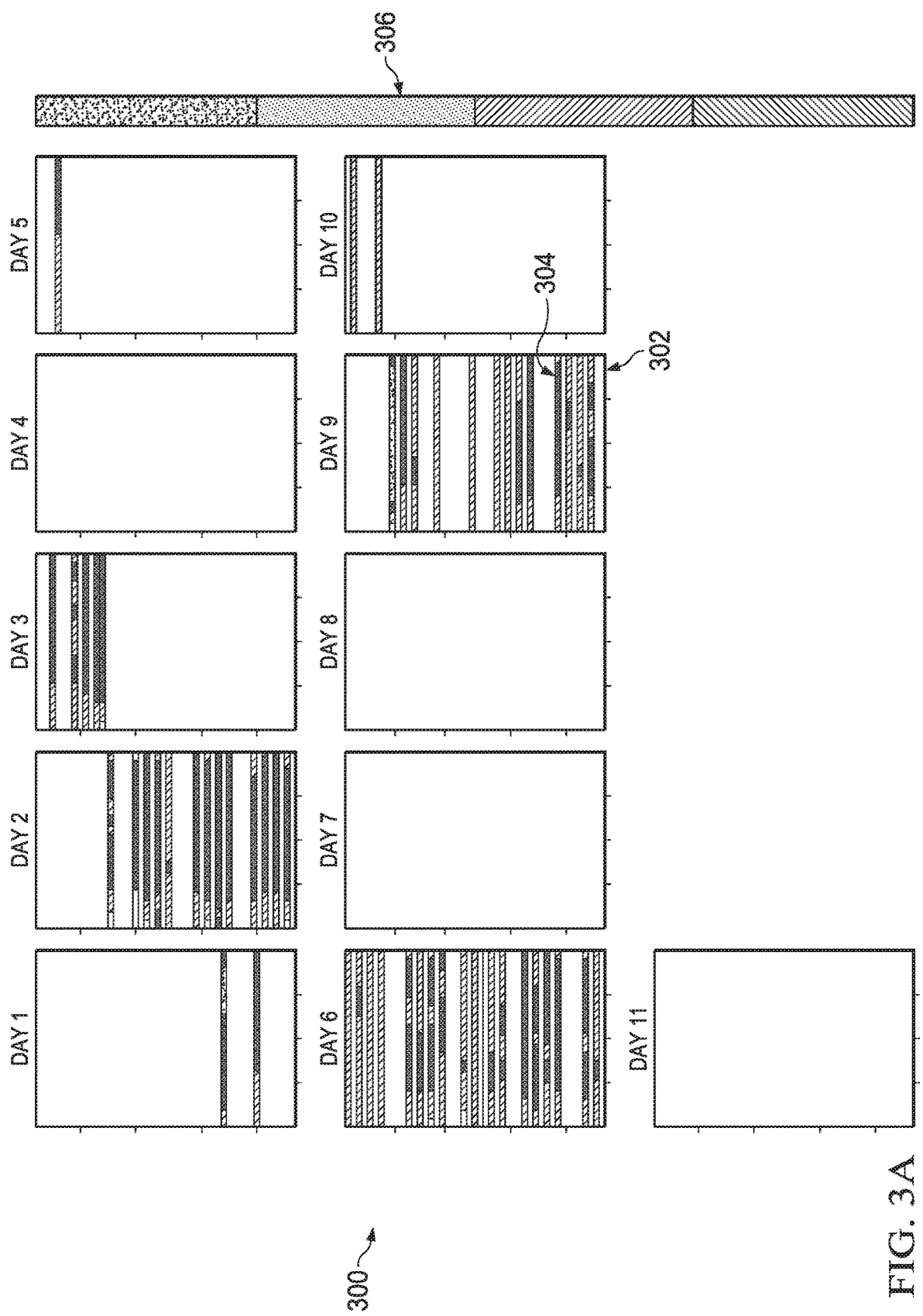
FIGS. 3A and 3B illustrate example observations and calculated projections of agricultural pests or diseases according to this disclosure.
Figure 3B:
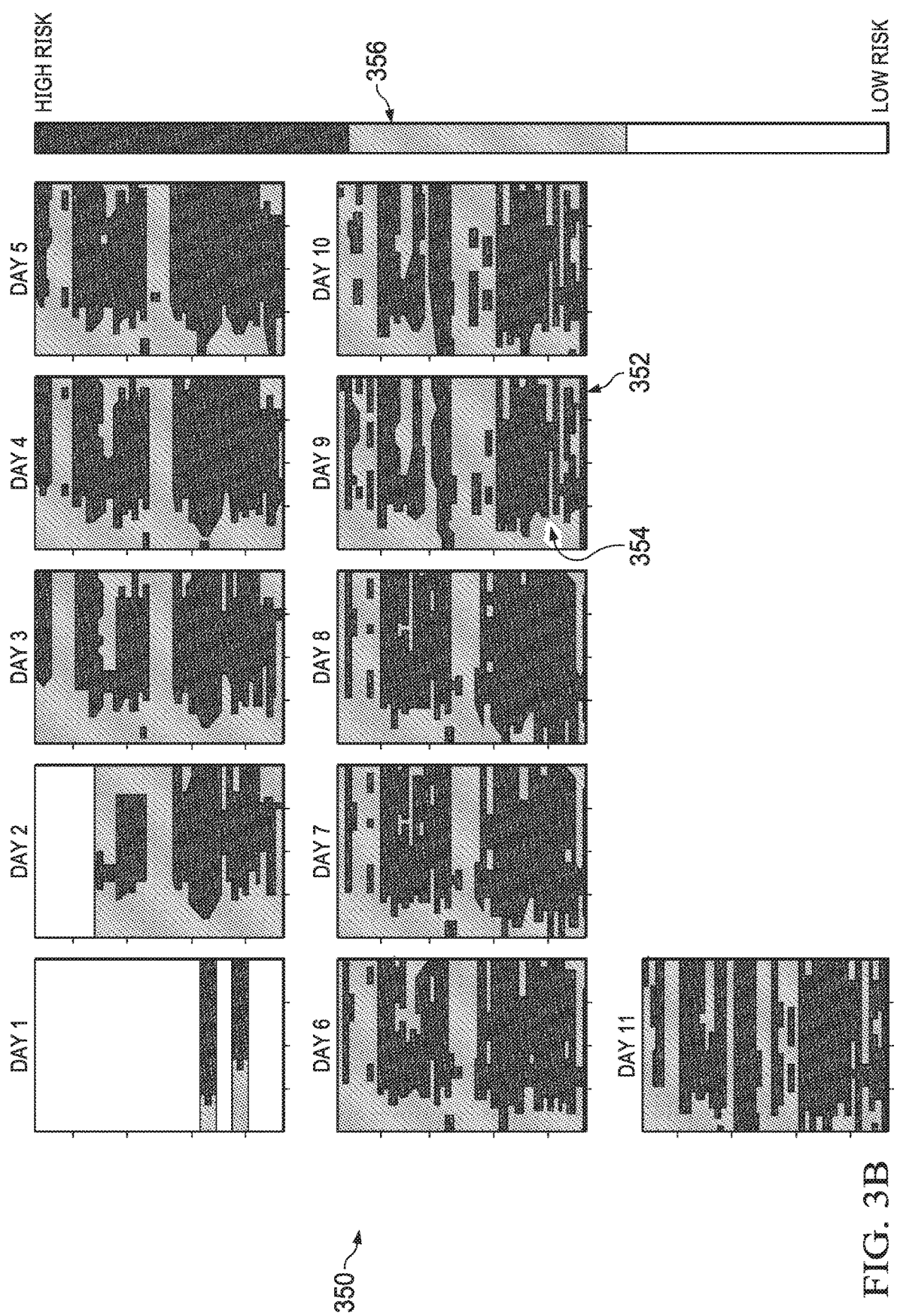

FIGS. 3A and 3B illustrate example observations 300 and calculated projections 350 of agricultural pests or diseases according to this disclosure. As shown in FIG. 3A, different collections 302 of individual observations 304 for at least a portion of a growing area 104 can be obtained by the data processing system 114. For example, the individual observations 304 may represent observed presences (and possibly quantities) of a particular pest in a specific growing area 104 or a portion of the growing area 104. Each individual observation 304 corresponds to a particular location in the growing area 104. The individual observations 304 may be obtained from one or more human scouts 106 (via one or more mobile electronic devices 108) and/or from one or more robotic scouts 110. As a particular example, the individual observations 304 may represent observed presences (and possibly quantities) of the particular pest in different rows of plants 102. A legend 306 is provided here to identify different pressure levels in the inspected locations of the growing area 104. The legend 306 here is provided for convenience only since the data forming the individual observations 304 need not include a legend 306.

In this example, each collection 302 represents the individual observations 304 captured by at least one human scout 106 and/or at least one robotic scout 110 during a specific day. Note, however, that other suitable time periods may be used. Blank areas in the different collections 302 represent portions of the growing area 104 that were not inspected on the associated days. Thus, for instance, the "Day 1," "Day 3," "Day 5," and "Day 10" collections 302 involved inspections of fewer rows of plants 102, the "Day 2," "Day 6," and "Day 9" collections 302 involved inspections of more numerous rows of plants 102, and the "Day 4," "Day 7," "Day 8," and "Day 11" collections 302 involved inspections of no rows of plants 102.

As shown in FIG. 3B, different collections 352 of individual projections 354 for the particular pest in at least the portion of the growing area 104 have been generated. These projections 354 are produced by the data processing system 114 using a spatiotemporal population projection model associated with the particular pest and the growing area 104. Each individual projection 354 corresponds to a particular location in the growing area 104.

Each collection 352 here represents the projected risk related to the particular pest as produced by the data processing system 114 based on the collection(s) 302 of individual observations 304 obtained up to that point in time. Thus, for example, the "Day 1" collection 352 represents the individual projections 354 for the particular pest generated by the data processing system 114 based on the "Day 1" collection 302 of observations 304. The "Day 2" collection 352 represents the individual projections 354 for the particular pest generated by the data processing system 114 based on the "Day 1" and "Day 2" collections 302 of observations 304. The "Day 3" collection 352 represents the individual projections 354 for the particular pest generated by the data processing system 114 based on the "Day 1," "Day 2," and "Day 3" collections 302 of observations 304. The "Day 11" collection 352 represents the individual projections 354 for the particular pest generated by the data processing system 114 based on the "Day 1" through "Day 10" collections 302 of observations 304. A legend 356 is provided here to identify different projected pressure levels in the various locations of the growing area 104. In some cases, at least one of the collections 352 may be presented to one or more users, in which case the legend 356 may be presented to the one or more users with the collection(s) 352.

The individual projections 354 generated in each collection 352 may be produced using a spatiotemporal population projection model commissioned for this particular pest and this particular growing area 104. The first several days of collections 352 of individual projections 354 have blank areas in this example. This is due to the fact that the first several days of collections 302 (the "Day 1" and "Day 2" collections 302) collectively contained observations 304 for some but not all locations in the growing area 104. By the third day, the data processing system 114 has obtained adequate data to identify the potential risk (pest pressure) for all locations in the growing area 104. At that point, for each day starting with the third day, the data processing system 114 is able to generate a risk or pressure map or other coverage map for the entire growing area 104, even though no single day in this example is associated with observations 304 of all locations in the entire growing area 104. Each collection 352 of individual projections 354 can be said to represent an estimated distribution of the particular pest in the inspected growing area 104. Thus, a series of collections 352 may represent changes in the estimated distribution of the particular pest in the inspected growing area 104 over time.

The collections 352 of individual projections 354 may be used in any suitable manner. For example, at least one collection 352 of individual projections 354 may be provided by the data processing system 114 to one or more mobile electronic devices 108 of one or more human scouts 106. This may help to inform the human scouts 106 of potential locations where the particular pest might be located, enabling the human scouts 106 to check those locations more carefully for the particular pest. As a particular example, at least one collection 352 of individual projections 354 may be presented to a human scout 106 via a web-based interface in order to allow the human scout 106 to plan his or her scouting pattern(s) in one or more growing areas 104 for the day. As another particular example, at least one collection 352 of individual projections 354 may be used by the data processing system 114 to send on-location notifications or alerts to a human scout 106 when the human scout 106 (or his or her electronic device 108) is detected to be at or near a location where at least one pest, disease, or biocontrol agent is projected to be located. At least one collection 352 of individual projections 354 may also be provided by the data processing system 114 to one or more robotic scouts 110, which may attempt to confirm whether the projections 354 are accurate. At least one collection 352 of individual projections 354 may further be provided to one or more additional users 118 for use in determining whether one or more treatments should be applied to at least one location in the growing area 104 or for use in reviewing the effectiveness of one or more treatments applied to at least one location in the growing area 104 (and whether any additional treatment should be applied). In addition, the data processing system 114 itself may use the collection(s) 352 to identify one or more treatments (or to review the effectiveness of one or more prior treatments and identify one or more additional treatments) and to automatically initiate the identified treatment(s) or make recommendations of the identified treatment(s) for consideration by the additional users 118. Other uses for the collections 352 are also possible, such as when used in estimating crop yields during crop productivity forecasting.

FIGS. 4A through 4D illustrate other example observations and calculated projections of agricultural pests, diseases, and biocontrol agents according to this disclosure. In particular, FIGS. 4A and 4B respectively illustrate example observations 400 and 420 of a particular pest and a particular biocontrol agent, and FIGS. 4C and 4D respectively illustrate example calculated projections 440 and 460 of the particular pest and the particular biocontrol agent. In this example, the observations and calculated projections are arranged in pairs, meaning the observations and calculated projections are associated with two related growing areas 104. For instance, the two related growing areas 104 may represent different halves or other related portions of a single greenhouse.

Figure 4A:
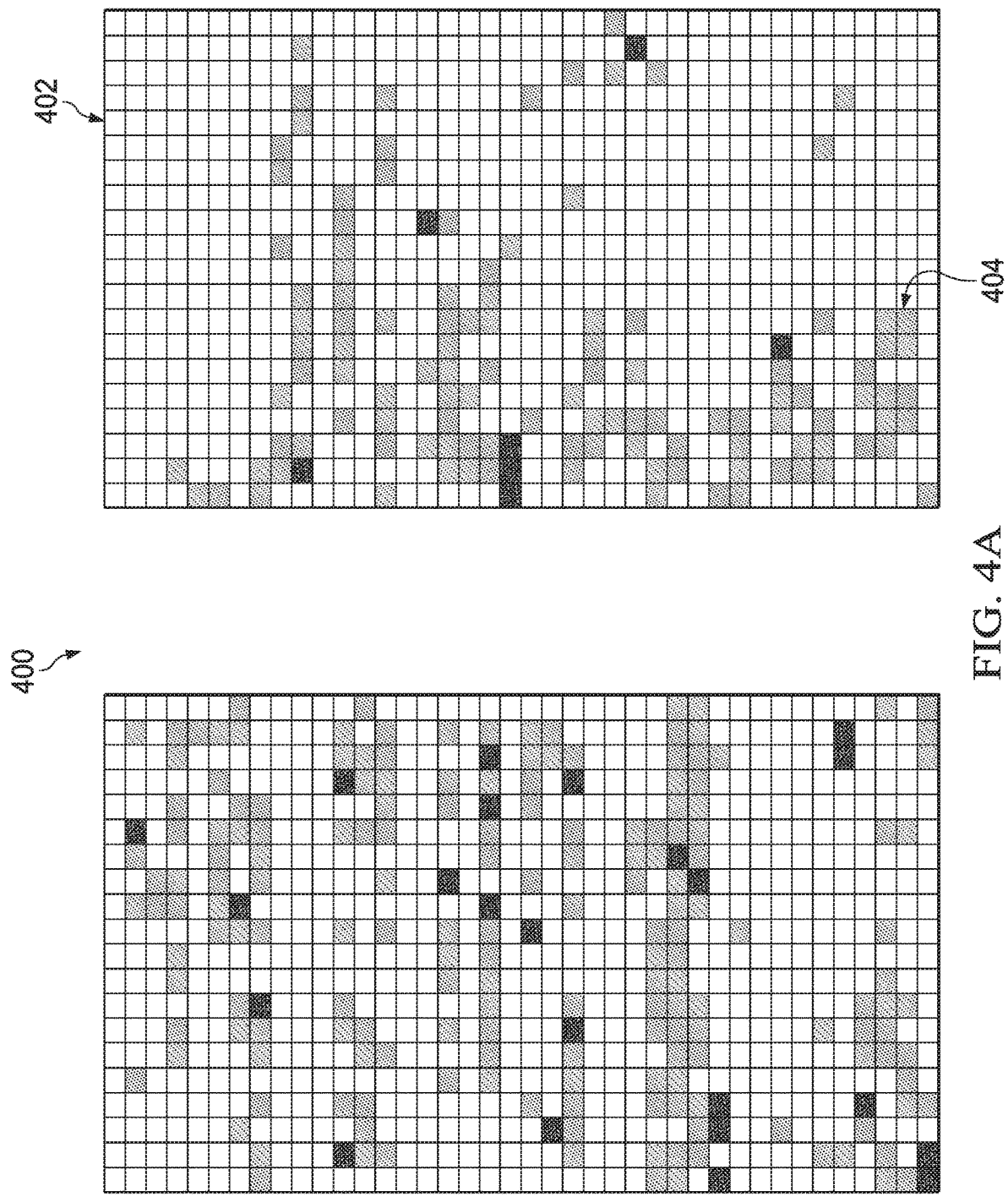
FIGS. 4A through 4D illustrate other example observations and calculated projections of agricultural pests, diseases, and biocontrol agents according to this disclosure.
Figure 4B:
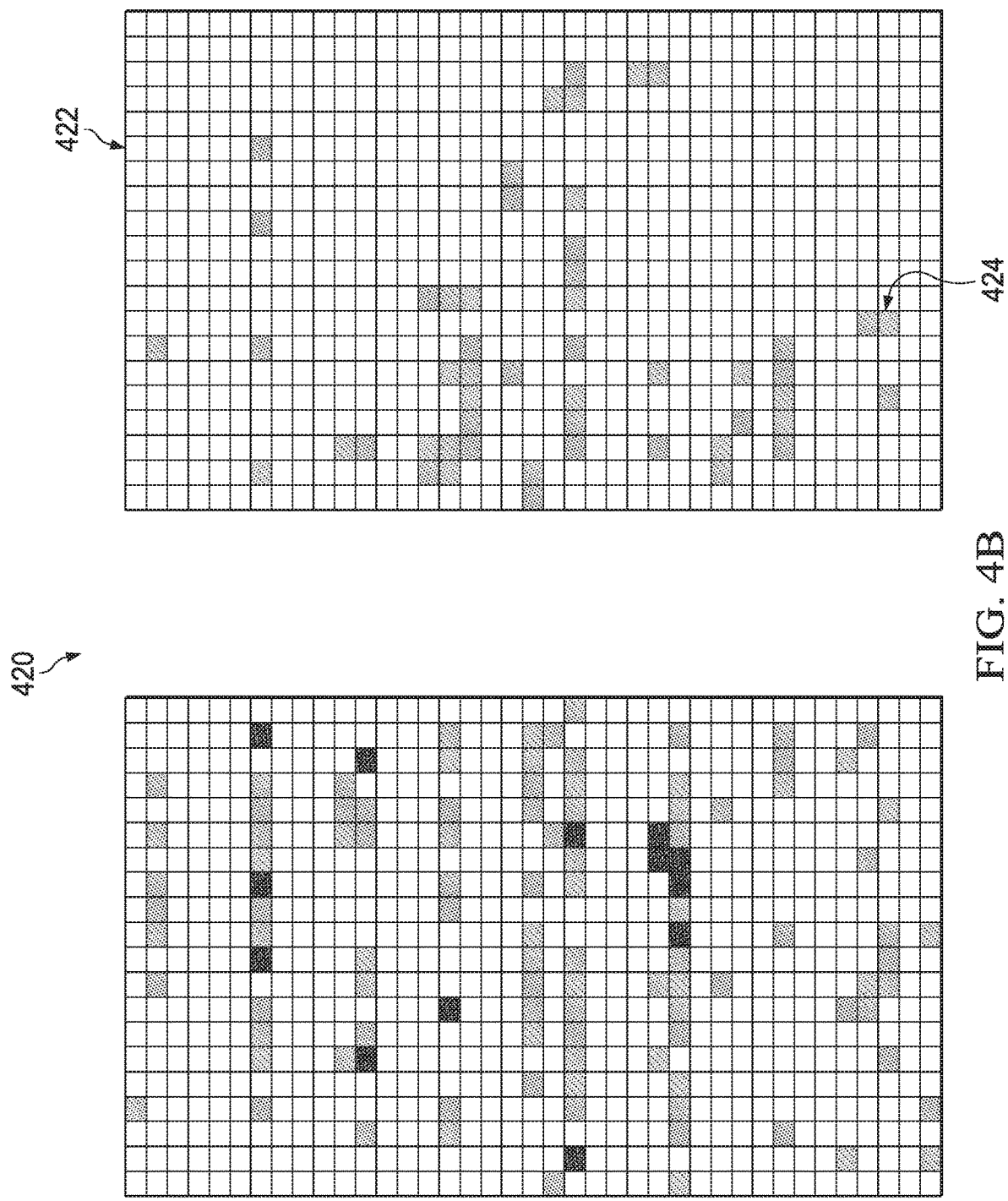

As shown in FIG. 4A, the observations 400 are arranged in a pair of grids 402, where different points in each grid 402 represent different locations in the pair of growing areas 104. Also, different indicators 404 are provided in each grid 402, and each indicator identifies the presence (and possibly the quantity) of a particular pest at the associated location in the pair of growing areas 104. Similarly, as shown in FIG. 4B, the observations 420 are arranged in a pair of grids 422, where different points in each grid 422 represent different locations in the pair of growing areas 104. Also, different indicators 424 are provided in each grid 422, and each indicator identifies the presence (and possibly the quantity) of a particular biocontrol agent (such as a beneficial organism) at the associated location in the pair of growing areas 104.

The information contained in the observations 400 and 420 may be obtained in any suitable manner, such as from one or more scouts 106, 110. Note that while only a single collection of observations 400 and a single collection of observations 420 are shown here, the data processing system 114 may obtain multiple collections of observations 400 and multiple collections of observations 420. These multiple collections of observations 400 and 420 may be obtained over multiple days or other time periods.

Figure 4C:
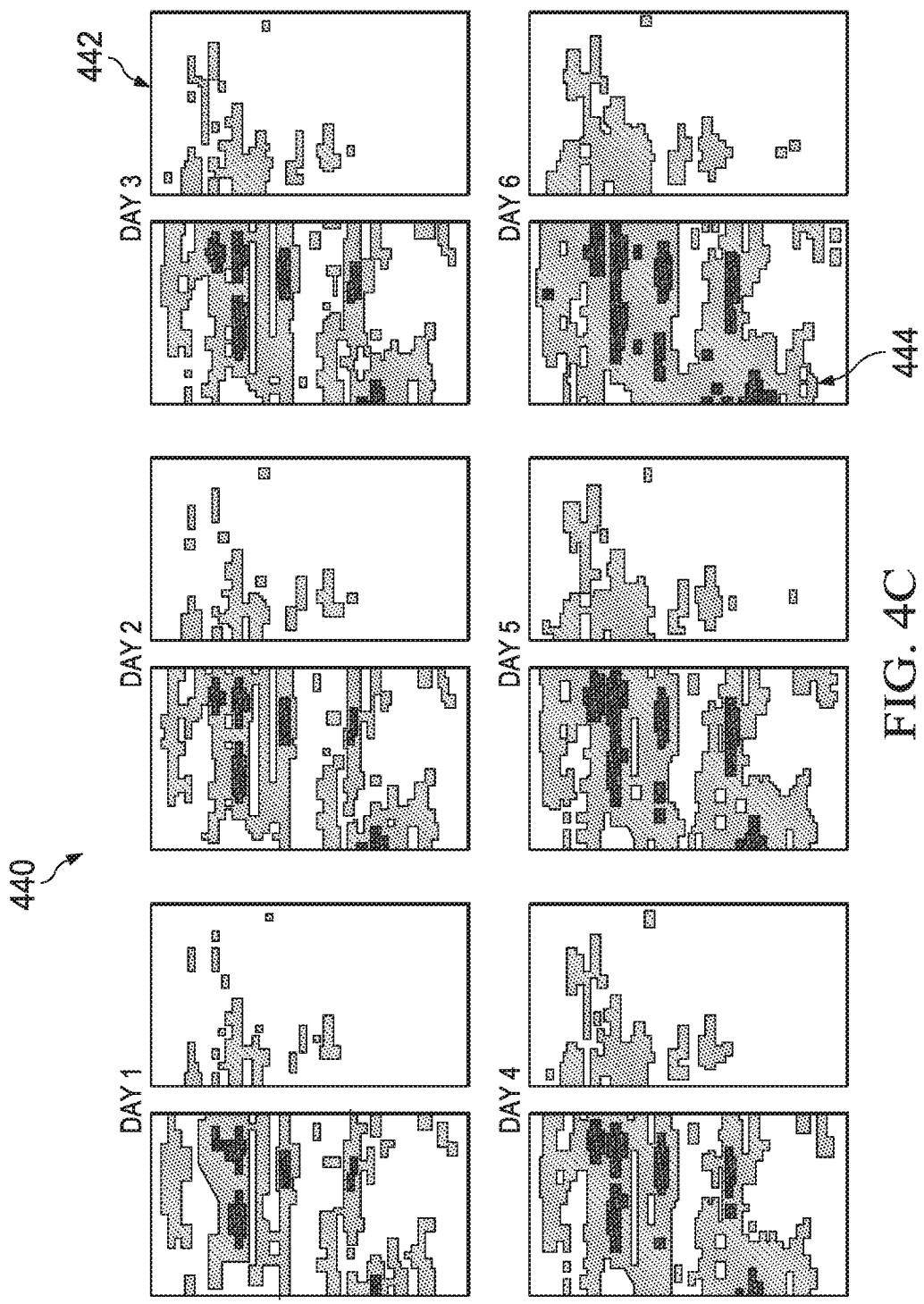
Figure 4D:
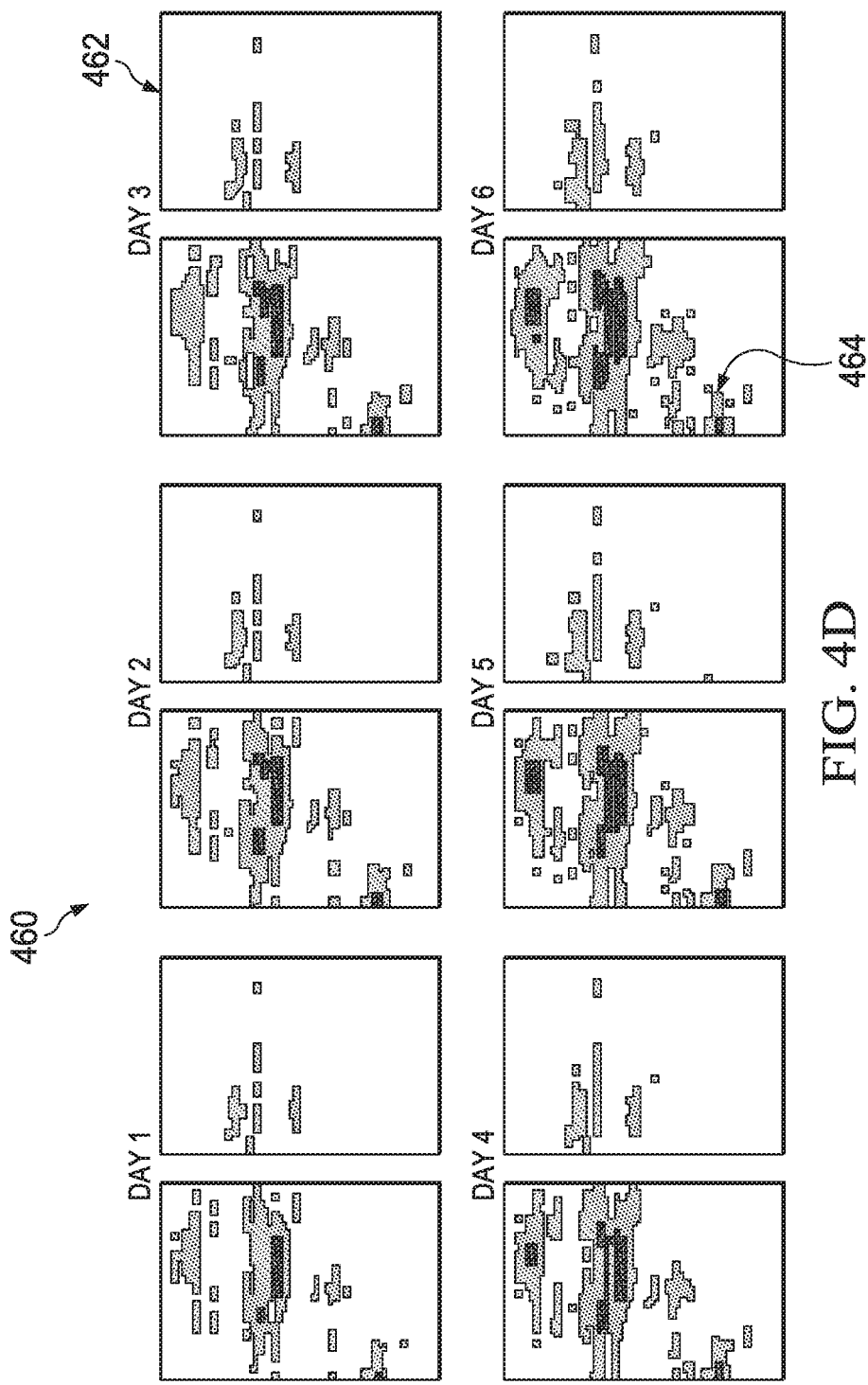

As shown in FIG. 4C, the calculated projections 440 are arranged in a pair of grids 442, where different points in each grid 442 represent different locations in the pair of growing areas 104. Also, different indicators 444 are provided in each grid 442, and each indicator identifies the calculated projection of the particular pest at the associated location in the pair of growing areas 104. Similarly, as shown in FIG. 4D, the calculated projections 460 are arranged in a pair of grids 462, where different points in each grid 462 represent different locations in the pair of growing areas 104. Also, different indicators 464 are provided in each grid 462, and each indicator identifies the calculated projection of the particular biocontrol agent (such as the beneficial organism) at the associated location in the pair of growing areas 104.

As can be seen here, both the particular pest and the particular biocontrol agent may spread and contract (often in relation to one another). Thus, it is possible in some cases for the data processing system 114 or one or more users to consider both the presence and extent of the particular pest and the biocontrol agent when making decisions regarding the growing areas 104. The calculated projections 440 and 460 here can span any suitable time period. The calculated projections 440 and 460 can also be used in any suitable manner (including the ways discussed above).

Note that the projections generated by the data processing system 114 for future time periods can be verified (or not verified) based on data collected by one or more scouts 106, 110. Thus, for instance, data from one or more scouts 106, 110 can be used to identify the actual presence (and possibly the actual quantity) or the actual absence of one or more pests and/or one or more beneficial organisms at various locations in one or more growing areas 104. This data can then be compared to the projections that the data processing system 114 generated for those same locations. Any differences produced by the comparisons can represent errors associated with the spatiotemporal population projection models being used by the data processing system 114. Among other things, this may allow the data processing system 114 or another component to identify the errors in the projections and to modify (or notify a user to recommission) one or more spatiotemporal population projection models being used by the data processing system 114.

Although FIGS. 3A through 4D illustrate examples of observations and calculated projections of agricultural pests, diseases, and biocontrol agents, various changes may be made to FIGS. 3A through 4D. For example, time periods other than days may be supported by the data processing system 114. Also, the specific contents of FIGS. 3A through 4D are for illustration only and are merely meant to illustrate examples of the types of operations that can be performed by the data processing system 114.

Figure 5:
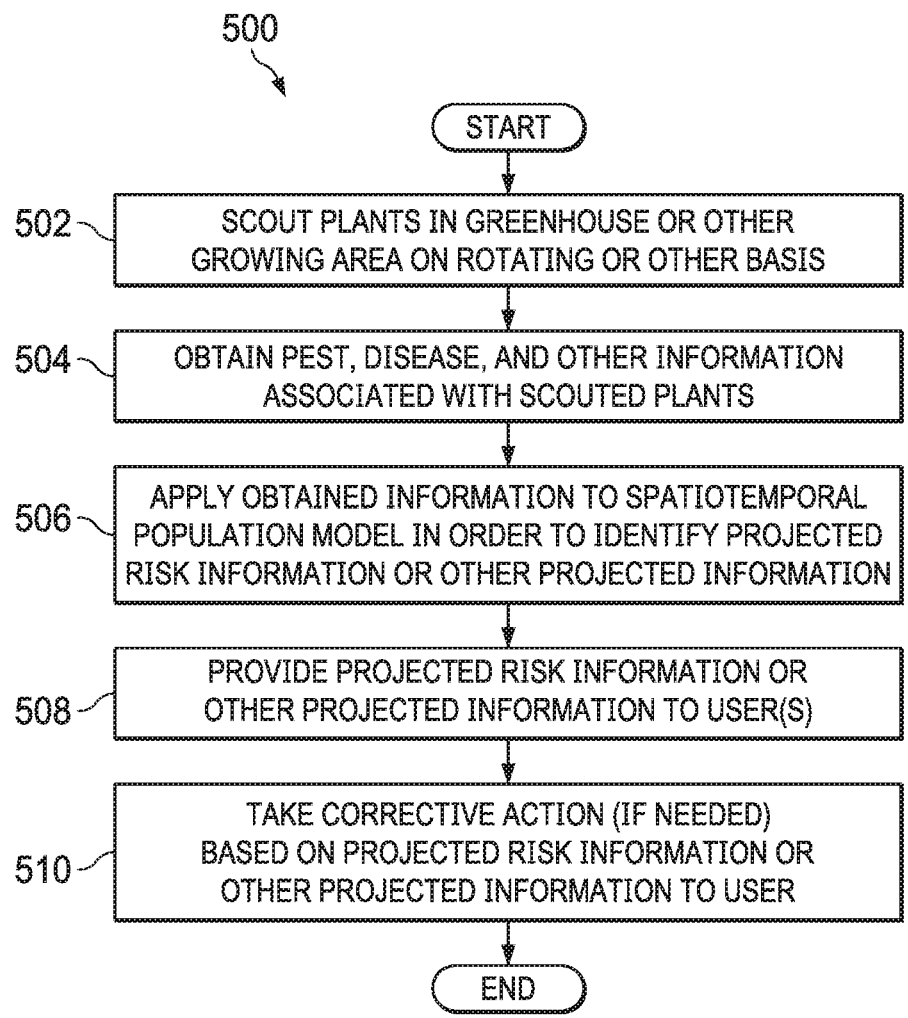
FIG. 5 illustrates an example method for real-time projections and estimated distributions of agricultural pests, diseases, and biocontrol agents according to this disclosure.

FIG. 5 illustrates an example method 500 for real-time projections and estimated distributions of agricultural pests, diseases, and biocontrol agents according to this disclosure. For ease of explanation, the method 500 shown in FIG. 5 may be described as involving the use of the data processing system 114 shown in FIG. 1, which may be implemented using at least one device 200 shown in FIG. 2. However, the method 500 may be performed by any other suitable devices in any other suitable systems.

As shown in FIG. 5, plants in at least one greenhouse or other growing area are scouted on a rotating basis or other basis at step 502. This may include, for example, one or more human scouts 106 and/or one or more robotic scouts 110 inspecting various plants 102 in at least one growing area 104. In some cases, the plants 102 may be inspected on a rotating basis, such as every two to five weeks. Spot inspections may also occur in random locations, and/or augmented inspections may also occur in locations where one or more pests or diseases were previously identified or projected to occur.

Pest information, disease information, and optionally other information associated with the scouted plants are obtained at step 504. This may include, for example, the data processing system 114 receiving data from the electronic device(s) 108 of the human scout(s) 106 and/or data from the robotic scout(s) 110. As particular examples, this may include the data processing system 114 receiving information identifying the presence (and possibly the quantity) of any pests, diseases, and optionally beneficial organisms or other biocontrol agents from the scout(s) 106, 110. The electronic device(s) 108, robotic scout(s) 110, data processing system 114, or other component may tag information about each specific plant 102 with the time/date that the information was captured and the location of the specific plant 102. Note that any other suitable information related to the plants 102 may be obtained here, such as information related to pollination of the plants 102 or abiotic stresses on the plants 102 (which may be due to a deficiency in fertilization or other causes).

The obtained information is applied to one or more spatiotemporal population projection models in order to identify projected risk information or other information associated with the plants at step 506. This may include, for example, the data processing system 114 applying the obtained information to a spatiotemporal population projection model for each pest, disease, and possibly biocontrol agent in each growing area 104 being monitored. The results of the processing can take various forms, such as a projection of how each pest, disease, or biocontrol agent might be distributed in each growing area 104 one or more days (or other time periods) into the future. This can be done for each pest/disease/biocontrol agent in each growing area 104.

The projected risk information or other information may be used in any suitable manner. For example, the projected risk information or other information may be provided to one or more users at step 508. This may include, for example, the data processing system 114 transmitting the projected risk information or other information to one or more electronic devices 108 of one or more human scouts 106. This may allow the human scouts 106 to know ahead of time which portions of each particular growing area 104 might have specific pests, diseases, or biocontrol agents. Among other things, this can help to improve the effectiveness of the human scouts 106 and allow less-experienced human scouts 106 to be used. This may also include the data processing system 114 transmitting the projected risk information or other information to one or more electronic devices 120 of one or more additional users 118. This may allow the additional users 118 to perform various functions, such as determining whether to apply one or more treatments to one or more growing areas 104 or portions thereof. As a particular example, actual and projected distributions of one or more pests, diseases, or biocontrol agents over time may be presented to the additional users 118 in order to provide insight into whether one or more pests or diseases are increasing or decreasing in one or more growing areas 104.

As another example, the projected risk information or other information may be used to identify and possibly initiate one or more corrective actions (if needed) at step 510. This may include, for example, the data processing system 114 using the projected risk information or other information to determine whether to initiate one or more treatments for one or more growing areas 104 or portions thereof. Any identified treatment may be initiated automatically or presented to one or more users (such as one or more additional users 118) for approval. In some instances, a heuristic may be used to determine whether to initiate one or more treatments, such as a heuristic that compares (for one, some, or all locations that might be treated in a growing area 104) whether the cost of the treatment outweighs the benefit that might be obtained at the location(s) using the treatment.

Although FIG. 5 illustrates one example of a method 500 for real-time projections and estimated distributions of agricultural pests, diseases, and biocontrol agents, various changes may be made to FIG. 5. For example, while shown as a series of steps, various steps in FIG. 5 may overlap, occur in parallel, occur in a different order, or occur any number of times. As a particular example, each plant 102 may be inspected at a prolonged interval (such as every two to five weeks), but the data processing system 114 may receive data, apply models, and generate projections much more frequently (such as daily).

In some embodiments, various functions described in this patent document are implemented or supported by a computer program that is formed from computer readable program code and that is embodied in a computer readable medium. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive (HDD), a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable storage device.

It may be advantageous to set forth definitions of certain words and phrases used throughout this patent document. The terms "application" and "program" refer to one or more computer programs, software components, sets of instructions, procedures, functions, objects, classes, instances, related data, or a portion thereof adapted for implementation in a suitable computer code (including source code, object code, or executable code). The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure, as defined by the following claims.

What is claimed is:

1. An apparatus comprising:
at least one processor configured to:
obtain multiple spatiotemporal population projection models, different spatiotemporal population projection models associated with different pests, diseases, or biocontrol agents in a growing area, each spatiotemporal population projection model defining how the associated pest, disease, or biocontrol agent spreads and contracts in the growing area over time;
receive information associated with an actual presence of a specific pest, disease, or biocontrol agent at one or more locations in the growing area, different locations in the growing area associated with different plants;
project a future presence of the specific pest, disease, or biocontrol agent in the growing area using the spatiotemporal population projection model associated with the specific pest, disease, or biocontrol agent, wherein, to project the future presence of the specific pest, disease, or biocontrol agent in the growing area, the at least one processor is configured to generate an estimated distribution of the specific pest, disease, or biocontrol agent across multiple monitored spatial locations in the growing area;
identify at least one treatment to be applied to one or more of the monitored spatial locations in the growing area based on the estimated distribution of the specific pest, disease, or biocontrol agent;
identify at least one additional treatment based on an effectiveness of the at least one treatment; and
control at least one actuator in order to initiate the at least one identified treatment and the at least one additional treatment.

2. The apparatus of claim 1, wherein each spatiotemporal population projection model defines, for each monitored spatial location in the growing area, an estimated pressure of the associated pest, disease, or biocontrol agent at that spatial location.

3. The apparatus of claim 2, wherein each spatiotemporal population projection model defines the estimated pressure of the associated pest, disease, or biocontrol agent at each monitored spatial location in the growing area based on:
a prior pressure of the associated pest, disease, or biocontrol agent at the spatial location;
a maximum limit of the associated pest, disease, or biocontrol agent at the spatial location;
a growth parameter defining how quickly the associated pest, disease, or biocontrol agent is able to grow and spread in the growing area;
a rate of overall change of all pressures of the associated pest, disease, or biocontrol agent in at least some monitored spatial locations in the growing area; and
one or more pressures of the associated pest, disease, or biocontrol agent in one or more neighboring spatial locations.

4. The apparatus of claim 3, wherein each spatiotemporal population projection model further defines the estimated pressure of the associated pest, disease, or biocontrol agent at each monitored spatial location in the growing area based on at least one of:
a climate in the growing area; and
a treatment applied to the spatial location.

5. The apparatus of claim 3, wherein each spatiotemporal population projection model is commissioned by selecting one or more parameters of the spatiotemporal population projection model to minimize errors between actual measurements of the associated pest, disease, or biocontrol agent and projected measurements of the associated pest, disease, or biocontrol agent.

6. The apparatus of claim 1, wherein the at least one processor is further configured to at least one of:
output the estimated distribution of the specific pest, disease, or biocontrol agent to at least one electronic device of at least one human scout; and
generate at least one notification or alert based on the estimated distribution of the specific pest, disease, or biocontrol agent and at least one location of the at least one human scout.

7. The apparatus of claim 1, wherein the at least one processor is further configured to output the estimated distribution of the specific pest, disease, or biocontrol agent to at least one electronic device of at least one user to provide insight into whether the specific pest, disease, or biocontrol agent is increasing or decreasing in the growing area and whether to apply the at least one treatment to one or more of the monitored spatial locations in the growing area.

8. The apparatus of claim 1, wherein the at least one processor is further configured to:
identify an effectiveness of at least one prior treatment previously applied to one or more of the monitored spatial locations in the growing area based on the estimated distribution of the specific pest, disease, or biocontrol agent; and
identify at least one second additional treatment to be applied to at least one of the monitored spatial locations in the growing area.

9. The apparatus of claim 1, wherein:
the spatiotemporal population projection models comprise first spatiotemporal population projection models; and
the at least one processor is further configured to:
obtain multiple second spatiotemporal population projection models associated with different pests, diseases, or biocontrol agents in a second growing area;
receive second information associated with an actual presence of a second specific pest, disease, or biocontrol agent at one or more second locations in the second growing area; and
project a future presence of the second specific pest, disease, or biocontrol agent in the second growing area using the second spatiotemporal population projection model associated with the second specific pest, disease, or biocontrol agent.

10. A non-transitory computer readable medium containing instructions that when executed cause at least one processor to:
obtain multiple spatiotemporal population projection models, different spatiotemporal population projection models associated with different pests, diseases, or biocontrol agents in a growing area, each spatiotemporal population projection model defining how the associated pest, disease, or biocontrol agent spreads and contracts in the growing area over time;

receive information associated with an actual presence of a specific pest, disease, or biocontrol agent at one or more locations in the growing area, different locations in the growing area associated with different plants;
project a future presence of the specific pest, disease, or biocontrol agent in the growing area using the spatiotemporal population projection model associated with the specific pest, disease, or biocontrol agent, wherein the instructions that when executed cause the at least one processor to project the future presence of the specific pest, disease, or biocontrol agent in the growing area comprise instructions that when executed cause the at least one processor to generate an estimated distribution of the specific pest, disease, or biocontrol agent across multiple monitored spatial locations in the growing area;
identify at least one treatment to be applied to one or more of the monitored spatial locations in the growing area based on the estimated distribution of the specific pest, disease, or biocontrol agent;
identify at least one additional treatment based on an effectiveness of the at least one treatment; and
control at least one actuator in order to initiate the at least one identified treatment and the at least one additional treatment.

11. The non-transitory computer readable medium of claim 10, wherein each spatiotemporal population projection model defines, for each monitored spatial location in the growing area, an estimated pressure of the associated pest, disease, or biocontrol agent at that spatial location.

12. The non-transitory computer readable medium of claim 11, wherein each spatiotemporal population projection model defines the estimated pressure of the associated pest, disease, or biocontrol agent at each monitored spatial location in the growing area based on:
a prior pressure of the associated pest, disease, or biocontrol agent at the spatial location;
a maximum limit of the associated pest, disease, or biocontrol agent at the spatial location;
a growth parameter defining how quickly the associated pest, disease, or biocontrol agent is able to grow and spread in the growing area;
a rate of overall change of all pressures of the associated pest, disease, or biocontrol agent in at least some monitored spatial locations in the growing area; and
one or more pressures of the associated pest, disease, or biocontrol agent in one or more neighboring spatial locations.

13. The non-transitory computer readable medium of claim 12, wherein each spatiotemporal population projection model further defines the estimated pressure of the associated pest, disease, or biocontrol agent at each monitored spatial location in the growing area based on at least one of:
a climate in the growing area; and
a treatment applied to the spatial location.

14. The non-transitory computer readable medium of claim 12, wherein each spatiotemporal population projection model is commissioned by selecting one or more parameters of the spatiotemporal population projection model to minimize errors between actual measurements of the associated pest, disease, or biocontrol agent and projected measurements of the associated pest, disease, or biocontrol agent.

15. The non-transitory computer readable medium of claim 7, further containing instructions that when executed cause the at least one processor to at least one of:
output the estimated distribution of the specific pest, disease, or biocontrol agent to at least one electronic device of at least one human scout; and
generate at least one notification or alert based on the estimated distribution of the specific pest, disease, or biocontrol agent and at least one location of the at least one human scout.

16. The non-transitory computer readable medium of claim 7, further containing instructions that when executed cause the at least one processor to output the estimated distribution of the specific pest, disease, or biocontrol agent to at least one electronic device of at least one user to provide insight into whether the specific pest, disease, or biocontrol agent is increasing or decreasing in the growing area and whether to apply the at least one treatment to one or more of the monitored spatial locations in the growing area.

17. The non-transitory computer readable medium of claim 7, further containing instructions that when executed cause the at least one processor to:
identify an effectiveness of at least one prior treatment previously applied to one or more of the monitored spatial locations in the growing area based on the estimated distribution of the specific pest, disease, or biocontrol agent; and
identify at least one second additional treatment to be applied to at least one of the monitored spatial locations in the growing area.

18. The non-transitory computer readable medium of claim 10, wherein:
the spatiotemporal population projection models comprise first spatiotemporal population projection models; and
further containing instructions that when executed cause the at least one processor to:
obtain multiple second spatiotemporal population projection models associated with different pests, diseases, or biocontrol agents in a second growing area;
receive second information associated with an actual presence of a second specific pest, disease, or biocontrol agent at one or more second locations in the second growing area; and
project a future presence of the second specific pest, disease, or biocontrol agent in the second growing area using the second spatiotemporal population projection model associated with the second specific pest, disease, or biocontrol agent.

19. A method comprising:
obtaining multiple spatiotemporal population projection models, different spatiotemporal population projection models associated with different pests, diseases, or biocontrol agents in a growing area, each spatiotemporal population projection model defining how the associated pest, disease, or biocontrol agent spreads and contracts in the growing area over time;
receiving information associated with an actual presence of a specific pest, disease, or biocontrol agent at one or more locations in the growing area, different locations in the growing area associated with different plants;
projecting, using at least one processing device, a future presence of the specific pest, disease, or biocontrol agent in the growing area using the spatiotemporal population projection model associated with the specific pest, disease, or biocontrol agent, wherein projecting the future presence of the specific pest, disease, or biocontrol agent in the growing area comprises generating an estimated distribution of the specific pest, disease, or biocontrol agent across multiple monitored spatial locations in the growing area;

identifying at least one treatment to be applied to one or more of the monitored spatial locations in the growing area based on the estimated distribution of the specific pest, disease, or biocontrol agent;

identifying at least one additional treatment based on an effectiveness of the at least one treatment; and controlling at least one actuator in order to initiate the at least one identified treatment and the at least one additional treatment.

20. The method of claim 19, wherein each spatiotemporal population projection model defines, for each monitored spatial location in the growing area, an estimated pressure of the associated pest, disease, or biocontrol agent at that spatial location.

21. The method of claim 20, wherein each spatiotemporal population projection model defines the estimated pressure of the associated pest, disease, or biocontrol agent at each monitored spatial location in the growing area based on:
 a prior pressure of the associated pest, disease, or biocontrol agent at the spatial location;
 a maximum limit of the associated pest, disease, or biocontrol agent at the spatial location;
 a growth parameter defining how quickly the associated pest, disease, or biocontrol agent is able to grow and spread in the growing area;
 a rate of overall change of all pressures of the associated pest, disease, or biocontrol agent in at least some monitored spatial locations in the growing area; and
 one or more pressures of the associated pest, disease, or biocontrol agent in one or more neighboring spatial locations.

22. The method of claim 21, wherein each spatiotemporal population projection model further defines the estimated pressure of the associated pest, disease, or biocontrol agent at each monitored spatial location in the growing area based on at least one of:
 a climate in the growing area; and
 a treatment applied to the spatial location.

23. The method of claim 21, wherein each spatiotemporal population projection model is commissioned by selecting one or more parameters of the spatiotemporal population projection model to minimize errors between actual measurements of the associated pest, disease, or biocontrol agent and projected measurements of the associated pest, disease, or biocontrol agent.

24. The method of claim 19, further comprising at least one of:
 outputting the estimated distribution of the specific pest, disease, or biocontrol agent to at least one electronic device of at least one human scout; and
 generating at least one notification or alert based on the estimated distribution of the specific pest, disease, or biocontrol agent and at least one location of the at least one human scout.

25. The method of claim 19, further comprising:
 outputting the estimated distribution of the specific pest, disease, or biocontrol agent to at least one electronic device of at least one user to provide insight into whether the specific pest, disease, or biocontrol agent is increasing or decreasing in the growing area and whether to apply the at least one treatment to one or more of the monitored spatial locations in the growing area.

26. The method of claim 19, further comprising:
 identifying an effectiveness of at least one prior treatment previously applied to one or more of the monitored spatial locations in the growing area based on the estimated distribution of the specific pest, disease, or biocontrol agent; and
 identifying at least one second additional treatment to be applied to at least one of the monitored spatial locations in the growing area.

27. The method of claim 19, wherein:
 the spatiotemporal population projection models comprise first spatiotemporal population projection models; and
further comprising:
 obtaining multiple second spatiotemporal population projection models associated with different pests, diseases, or biocontrol agents in a second growing area;
 receiving second information associated with an actual presence of a second specific pest, disease, or biocontrol agent at one or more second locations in the second growing area; and
 projecting a future presence of the second specific pest, disease, or biocontrol agent in the second growing area using the second spatiotemporal population projection model associated with the second specific pest, disease, or biocontrol agent.

* * * * *